US012655097B2

(12) United States Patent
Lee et al.

(10) Patent No.: US 12,655,097 B2
(45) Date of Patent: Jun. 16, 2026

(54) PROCESSES FOR REMOVING CARBON DISULFIDE FROM SULFIDE PRODUCT STREAMS

(71) Applicant: Chevron Phillips Chemical Company LP, The Woodlands, TX (US)

(72) Inventors: Jeremy Lee, Borger, TX (US); Brian G. Gerlach, Borger, TX (US); Dale M. Solaas, Borger, TX (US); Kenneth M. Lassen, Bartlesville, OK (US); Ugochukwu Nwagwu, Kingwood, TX (US); Jonathan A. Powell, Kingwood, TX (US); Daniel M. Hasenberg, Kingwood, TX (US)

(73) Assignee: Chevron Phillips Chemical LP, The Woodlands, TX (US)

( * ) Notice: Subject to any disclaimer, the term of this patent is extended or adjusted under 35 U.S.C. 154(b) by 0 days.

(21) Appl. No.: 19/092,612

(22) Filed: Mar. 27, 2025

(65) Prior Publication Data

US 2025/0304530 A1 Oct. 2, 2025

Related U.S. Application Data

(60) Provisional application No. 63/571,767, filed on Mar. 29, 2024.

(51) Int. Cl.
*C07C 319/28* (2006.01)
*B01D 11/04* (2006.01)

(52) U.S. Cl.
CPC ........ *C07C 319/28* (2013.01); *B01D 11/0492* (2013.01)

(58) Field of Classification Search
CPC ............................ C07C 319/28; C07C 321/14
USPC ............................................................ 568/59
See application file for complete search history.

(56) References Cited

U.S. PATENT DOCUMENTS

| | | | |
|---|---|---|---|
| 6,736,879 B2 * | 5/2004 | Hasenberg | B01D 53/04 |
| | | | 95/135 |
| 2006/0140852 A1 * | 6/2006 | Russell | C01B 3/38 |
| | | | 423/652 |
| 2016/0207854 A1 | 7/2016 | Weissheimer et al. | |
| 2024/0083841 A1 | 3/2024 | Lassen et al. | |

FOREIGN PATENT DOCUMENTS

| | | |
|---|---|---|
| GB | 572690 A | 10/1945 |
| WO | WO2020/223035 | * 11/2020 |

OTHER PUBLICATIONS

International Search Report and Written Opinion of the International Searching Authority for International Patent Application No. PCT/US2025/021797, Jul. 22, 2025, 9 pages.
Declaration of Mr. Jeremy Lee, Feb. 6, 2026, 2 pages.

* cited by examiner

*Primary Examiner* — Ana Z Muresan
(74) *Attorney, Agent, or Firm* — Merchant & Gould, P.C.

(57) ABSTRACT

Processes for removing carbon disulfide from product streams containing a sulfide compound are performed by contacting the product stream with an aqueous solution comprising a mercaptide to form a mixture, or by contacting the product stream with an aqueous solution comprising a mercaptan and a base to form a mixture. An aqueous layer is removed from the mixture, resulting in a high purity sulfide stream with significantly less carbon disulfide.

23 Claims, 3 Drawing Sheets

PROCESSES FOR REMOVING CARBON DISULFIDE FROM SULFIDE PRODUCT STREAMS

REFERENCE TO RELATED APPLICATION

This application claims the benefit of U.S. Provisional Patent Application No. 63/571,767, filed on Mar. 29, 2024, the disclosure of which is incorporated herein by reference in its entirety.

FIELD OF THE INVENTION

Sulfide compounds such as dimethyl sulfide have wide industrial application, for instance as a sulfidation agent in steam cracking production of olefins like ethylene and propylene where sulfidation of furnace tube walls mitigates coke formation and carbon monoxide production, as gas odorants, and in the production of dimethyl sulfoxide. Impurities such as carbon disulfide can accumulate in sulfide product streams, for instance as a byproduct of industrial scale production of methyl mercaptan. The presence of carbon disulfide limits the industrial application of dimethyl sulfide product streams. The present disclosure generally relates to the removal of impurities such as carbon disulfide ($CS_2$) from product streams containing sulfide compounds.

BACKGROUND OF THE INVENTION

Product streams containing sulfide compounds also can contain impurities that are difficult to remove from the product streams directly. Impurities such as carbon disulfide that have similar physical or chemical attributes to the product sulfide compound, can be particularly difficult to separate from the product stream. Moreover, removal of impurities beyond a certain degree may require conditions that can be commercially impractical for large-scale production operations. Thus, it would be beneficial to develop processes that can improve the efficiency and effectiveness of removing sulfide impurities from product streams containing sulfide compounds. Accordingly, it is to these ends that the present invention is generally directed.

SUMMARY OF THE INVENTION

Figure 1:
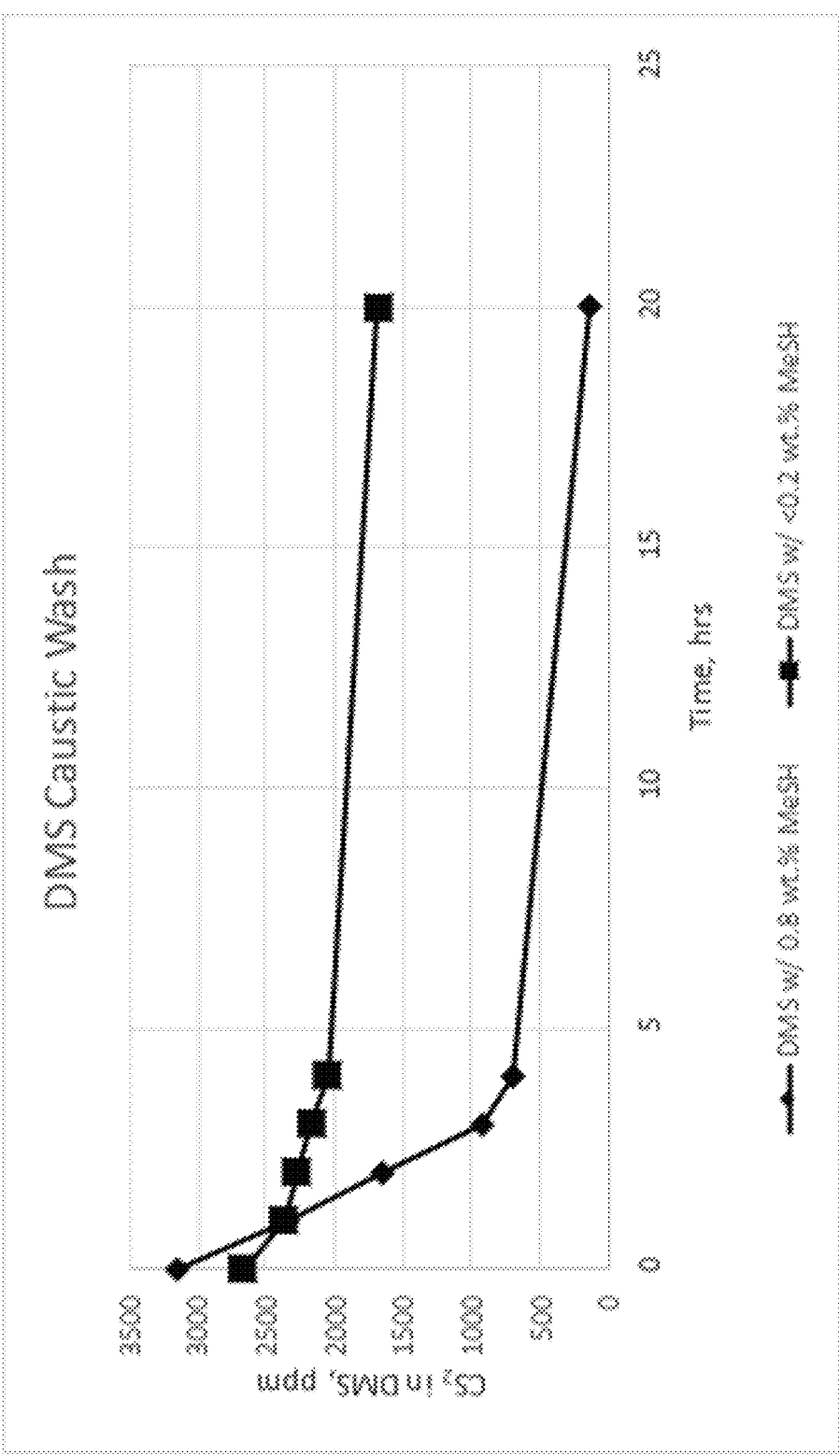
FIG. 1 presents a graph showing the decrease in $CS_2$ content over time for Examples 3 and 4.

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

The invention disclosed herein generally relates to processes for purifying a product stream containing a sulfide compound and $CS_2$. The processes can comprise (i) contacting the product stream with an aqueous solution of a mercaptan and a base to form a mixture, and (ii) removing at least a portion of an aqueous layer from the mixture to form a purified sulfide stream. In certain aspects, processes can further comprise a step of (iii) drying the purified sulfide stream to form a dried sulfide product stream.

These processes can be applied to product streams containing a sulfide compound having formula (I):

$$R^1\text{---}S\text{---}R^2. \tag{I}$$

Generally, $R^1$ and $R^2$ independently can be a $C_1$ to $C_{18}$ substituted or unsubstituted, cycloalkyl group or linear or branched alkyl group. In certain aspects, the sulfide compound can be dimethyl sulfide.

Processes disclosed herein can form purified sulfide streams having low levels of carbon disulfide. For instance, the processes disclosed herein can have a ratio of the concentration of $CS_2$ present in the product stream prior to step (i) to the concentration of $CS_2$ present in the purified sulfide stream of at least 100:1—thus, a 100-fold reduction in the $CS_2$ concentration.

Optionally, the processes disclosed herein can further comprise the steps of determining a concentration of the $CS_2$ in the product stream and adjusting an amount of the mercaptan contacted with the product stream based on the concentration of the $CS_2$ in the product stream. Similarly, the processes disclosed herein can further comprise the steps of determining a concentration of the $CS_2$ in the purified sulfide stream and adjusting an amount of the mercaptan contacted with the product stream based on the concentration of the $CS_2$ in the purified sulfide stream.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

Herein, features of the subject matter can be described such that, within particular aspects and/or embodiments, a combination of different features can be envisioned. For each and every aspect, and/or embodiment, and/or feature disclosed herein, all combinations that do not detrimentally affect the designs, processes, and/or methods described herein are contemplated with or without explicit description of the particular combination. Additionally, unless explicitly recited otherwise, any aspect, and/or embodiment, and/or feature disclosed herein can be combined to describe inventive features consistent with the present disclosure.

While compositions and processes are described in terms of "comprising" various components or steps, the compositions and methods also can "consist essentially of" or "consist of" the various components or steps, unless specifically stated otherwise.

The terms "a," "an," and "the" are intended to include plural alternatives, e.g., at least one, unless otherwise specified. For instance, the disclosure of "a sulfide" and "a mercaptide" is meant to encompass one, or mixtures or combinations of more than one, sulfide and mercaptan, respectively, unless otherwise specified.

All "ppm" quantities disclosed herein refer to ppm by weight (or ppmw), unless specifically stated otherwise.

For any particular compound or group disclosed herein, any name or structure presented is intended to encompass all conformational isomers, regioisomers, and stereoisomers that can arise from a particular set of substituents, unless otherwise specified. For example, a general reference to pentane includes n-pentane, 2-methyl-butane, and 2,2-dimethylpropane, and a general reference to a butyl group includes an n-butyl group, a sec-butyl group, an iso-butyl group, and a t-butyl group. The name or structure also encompasses all enantiomers, diastereomers, and other optical isomers whether in enantiomeric or racemic forms, as well as mixtures of stereoisomers, as would be recognized by a skilled artisan, unless otherwise specified.

The term "substituted" when used to describe a group, for example, when referring to a substituted analog of a particular group, is intended to describe any non-hydrogen moiety that formally replaces a hydrogen in that group and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

In the context of this disclosure, the term "mercaptan" will be understood to include all ionic states of a particular compound containing a thiol group. As used herein, an amount of "mercaptan" in solution therefore will include any amount of the protonated mercaptan and any amount of the unprotonated thiolate anion. Accordingly, references to a molar ratio of mercaptan:$CS_2$ in the mixture formed by step (i) considers the total amount of mercaptan and thiolate anion present in the mixture, independently from the pH of the mixture or protonation state of the respective species. Similarly, reference to "mercaptide" will be understood to refer to the amount of a mercaptan salt present either as an ion pair, or as a thiolate anion in solution. In contrast, reference to a "thiolate" (e.g., methanethiolate) or "thiolate anion" will refer only to the amount of the ionized species present. Thus, an aqueous solution comprising a mercaptan and a base can be formed by addition of a mercaptide to water, thereby forming an amount of the thiolate anion in the solution.

The terms "contacting" and "combining" are used herein to describe methods and processes in which the materials or components are contacted or combined together in any order, in any manner, and for any length of time, unless otherwise specified. For example, the materials or components can be blended, mixed, slurried, dissolved, reacted, treated, compounded, impregnated, or otherwise contacted or combined in some other manner or by any suitable method or technique.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a moiety is a $C_1$ to $C_{12}$ hydrocarbyl group, or in alternative language, a hydrocarbyl group having from 1 to 12 carbon atoms, as used herein, refers to a moiety that can have 1, 2, 3, 4, 5, 6, 7, 8, 9, 10, 11, or 12 carbon atoms, as well as any range between these two numbers (for example, a $C_2$ to $C_6$ hydrocarbyl group), and also including any combination of ranges between these two numbers (for example, a $C_2$ to $C_4$ and a $C_8$ to $C_{12}$ hydrocarbyl group).

Similarly, another representative example follows for the molar ratio of methanethiolate:$CS_2$ employed in aspects of step (i) of the disclosed processes. By a disclosure that the molar ratio of methanethiolate:$CS_2$ can be in a range from 1:1 to 6:1, the intent is to recite that the ratio of methanethiolate:$CS_2$ can be any ratio in the range and, for example, can be equal to 1:1, 1.5:1, 2:1, 3:1, 4:1, 5:1, or 6:1. Additionally, the ratio of methanethiolate:$CS_2$ can be within any range from 1:1 to 6:1 (for example, from 2:1 to 6:1), and this also includes any combination of ranges between 1:1 and 6:1 (for example, the methanethiolate:$CS_2$ ratio can be in a range from 3:1 to 4:1, or from 5:1 to 6:1).

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Many product streams containing sulfide compounds also contain impurities that are both difficult to remove and limit the ability of the sulfide product stream to be used in a variety of desirable end-use applications. For instance, dimethyl sulfide product streams often contain 1000-4000 ppmw by weight of carbon disulfide ($CS_2$). While the purity of the dimethyl sulfide in the product stream is very high (e.g., greater than 98 wt. %, and often greater than 99 wt. %), ppmw amounts of carbon disulfide present in the dimethyl sulfide product stream can prevent it from being used in end-use applications that require substantially "pure" dimethyl sulfide, generally requiring ppmw amounts of carbon disulfide of less than 100 ppmw, and in some cases, less than 20 ppmw. However, removal of carbon disulfide ($CS_2$) from dimethyl sulfide using conventional separations techniques is not feasible. Distillation, for instance, cannot approach the very low ppmw levels of carbon disulfide needed to produce substantially pure dimethyl sulfide because the volatility difference between $CS_2$ and DMS approaches zero at low $CS_2$ concentrations. Caustic washing of DMS with an aqueous NaOH solution also does not remove $CS_2$ from DMS. Thus, alternative means for eliminating difficult-to-remove impurities from such sulfide product streams are needed.

Processes for Removing $CS_2$ from Product Streams Comprising Sulfide Compounds

Accordingly, disclosed herein are alternative processes for purifying product streams comprising (or consisting essentially of, or consisting of) a sulfide compound and carbon disulfide ($CS_2$). Such processes can comprise (or consist essentially of or consist of) (i) contacting the product stream with an aqueous solution of a mercaptan and a base to form a mixture, and (ii) removing at least a portion of an aqueous layer from the mixture to form a purified sulfide stream. Processes disclosed herein can further comprise a step of (iii) drying the purified sulfide stream to form a dried sulfide product stream. Where included, the drying step can comprise techniques can include heating, evaporating, distilling, and the like, or any combination of two or more of these techniques. Processes may further comprise additional purification steps, for instance filtration, or additional extraction steps.

Generally, the features of the processes (e.g., the components and/or features of the product stream, the mercaptide, the components and/or features of the purified sulfide stream, and the process conditions under which the product stream and mercaptide are contacted, among others) are independently described herein, and these features can be combined in any combination to further describe the disclosed purification processes.

The amount of the sulfide compound present in the product stream is not particularly limited, although the sulfide compound generally constitutes the vast majority of the product stream, for instance, at least 80 wt. %, at least 85 wt. %, or at least 90 wt. %, and more often, the product stream contains at least 95 wt. %, at least 98 wt. %, at least 99 wt. %, or at least 99.9 wt. %, of the sulfide compound. Representative ranges for the amount of the sulfide compound in the product stream can include from 90 wt. % to 99.99 wt. %, from 95 wt. % to 99.99 wt. %, from 98 wt. % to 99.9 wt. %, or from 99 wt. % to 99.9 wt. %. Thus, the product stream can be a relatively pure sulfide product stream containing only trace amounts of certain impurities, and the impurities can be difficult to remove by conventional purification processes.

The product stream also can contain an unacceptably high amount of carbon disulfide. In some aspects, the product stream prior to step (i) can contain from 100 ppmw to 10,000 ppmw (by weight) of carbon disulfide, such as from 250 ppmw to 5000 ppmw, from 500 ppmw to 10,000 ppmw, from 1000 ppmw to 5000 ppmw, or from 2000 ppmw to 4000 ppmw, or from 1500 ppmw to 3000 ppmw, although not limited thereto. In other aspects, the amount of carbon disulfide present in the product stream can be at least 100 ppmw, at least 250 ppmw, at least 500 ppmw, at least 1000 ppmw, or at least 2000 ppmw (by weight).

The product stream also can contain additional impurities and by-products from the production of the sulfide compound. Such additional impurities can further complicate the purification of the product stream. As an example, the product stream can comprise an amount of methyl mercaptan, an amount of dimethyl disulfide, and/or an amount of water prior to step (i). Where present, the product stream can contain an amount of methyl mercaptan in a range from 10 ppmw to 1000 ppmw, from 50 ppmw to 500 ppmw, or from 10 ppmw to 100 ppmw. Similarly, the product stream can contain an amount of dimethyl disulfide in a range from 10 ppmw to 1000 ppmw, from 50 ppmw to 500 ppmw, or from 10 ppmw to 100 ppmw. Further still, the product stream can contain an amount of water in a range from 10 ppmw to 1000 ppmw, from 50 ppmw to 500 ppmw, or from 10 ppmw to 100 ppmw. In certain aspects, the amount of impurities other than carbon disulfide (e.g., methyl mercaptan, dimethyl disulfide, water) in the purified sulfide stream independently can be unchanged, less than, or greater than that in the product stream containing the sulfide compound.

In step (i), the aqueous solution of the mercaptan and the base generally can be formed by the simple addition of a mercaptan and a base to water, in any order. Alternatively, the aqueous solution of the mercaptan and the base can be formed by addition of a mercaptide to water, thereafter dissociating to the base and the thiolate anion in certain proportions based on the resulting pH and $pK_a$ of the mercaptan. In certain aspects, the mercaptide can be an ion pair comprising an alkylthiolate anion and an alkali metal cation (e.g., sodium, potassium). For instance, sodium methyl mercaptide can be added directly to water. Alternatively, an aqueous solution of a mercaptan and a base, e.g., sodium hydroxide, potassium hydroxide, calcium hydroxide, ammonium hydroxide, or any combination thereof. In one aspect, an aqueous solution of methyl mercaptan and sodium hydroxide gives rise to the aqueous solution of the mercaptide, sodium methyl mercaptide.

As those of skill in the art would appreciate, the sodium methyl mercaptide thus formed in basic solution can be present predominantly as methanethiolate anion, with equilibrium concentration determined by the pH of the aqueous solution. In certain aspects, the pH of the aqueous solution comprising the mercaptide can be at least 8, at least 9, at least 9.5, at least 10, at least 10.5, at least 11, at least 11.5, or at least 12; alternatively, in a range from 8 to 14, from 9 to 14, from 10 to 14, or from 10 to 13.

Any suitable temperature and pressures conditions can be used for step (i). The temperature is not particularly limited, and generally can be any temperature sufficient and practical for mixing and subsequent separation of the aqueous phase and organic phase formed in step (i). For instance, step (i) can be conducted without heating, at ambient temperature. In other aspects, the temperature of step (i) can be in a range from 0° C. to 40° C., from 10° C. to 35° C., or from 15° C. to 30° C. Similarly, the pressure in step (i) is not particularly limited, but in some aspects, can be such that each component of the product stream remains a liquid at the operating temperature. Thus, step (i) can be conducted at ambient pressure or a pressure of at least 5 psig, at least 10 psig, at least 15 psig, at least 20 psig, at least 25 psig, at least 30 psig, at least 40 psig, at least 50 psig, at least 60 psig, at least 80 psig, or at least 100 psig. In some aspects, step (i) can be conducted at a pressure in a range from ambient pressure to 100 psig, or from 5 psig to 60 psig. Suitable temperatures and pressures employed in the processes disclosed herein can preferentially maintain the components of the mixture in a liquid state. It will be understood by those of skill in the art where temperatures may exceed the boiling point of a certain component, the pressure may be adjusted accordingly to ensure the mixture remains in a liquid state. Thus, in certain aspects under appropriate pressure, the temperature of step (i) can be in a range from 15° C. to 85° C., from 20° C. to 70° C., from 25° C. to 60° C., or from 30° C. to 45° C.

Any suitable relative amount of the mercaptan can be used in step (i). For instance, the amount of mercaptan can be determined relative to the amount of $CS_2$ in the product stream. In certain aspects, the molar ratio defined as mercaptan:$CS_2$ can be in a range from 1:1 to 100:1, from 1:1 to 50:1, from 1.5:1 to 50:1, from 1.5:1 to 30:1, from 2:1 to 20:1, or from 3:1 to 10:1.

It also can be beneficial to use an excess of the mercaptan relative to the amount of carbon disulfide impurity in the product stream, as a concentration of the mercaptide in the aqueous phase. The concentration of mercaptan within the aqueous phase can be in any suitable amount. In some aspects, the concentration of the mercaptan in the aqueous phase added to the product stream can be in a range from 0.01 to 25 wt. %, from 1 to 30 wt. %, from 2 to 25 wt. %, from 3 to 20 wt. %, or from 5 to 15 wt. %, based on the weight of the aqueous phase added to the product stream.

Step (i) can be conducted for any suitable period of time, generally for a time period sufficient for substantially all of the $CS_2$ to be extracted from the product stream and into the aqueous phase of the mixture. Although the particular time can vary based on the concentration of mercaptide in the aqueous phase and the amount of the aqueous phase, among other variables, step (i) often can be conducted for a time period in a range from 1 min to 24 hr, from 30 min to 24 hr, from 1 hr to 12 hr, from 2 hr to 8 hr, or from 3 hr to 5 hr, and the like. To improve the contact between the $CS_2$ present in the product stream and the mercaptide within the aqueous solution, the mixture of the product stream (containing $CS_2$) and the aqueous solution of the mercaptide can be vigorously agitated in step (i).

Following satisfactory interaction between the product stream and the aqueous solution of the mercaptan and the base has been achieved in step (i), at least a portion of the aqueous layer containing the $CS_2$ impurity can be removed from the mixture formed in step (i). Removing the aqueous layer from the mixture to form the purified sulfide stream can be accomplished by any suitable and practical methodology, including but not limited to extracting, centrifuging, filtering, decanting, draining, evaporating, distilling, or any combination thereof. In certain aspects, the aqueous layer may be completely removed from the mixture. In other aspects, the aqueous layer may form the denser portion of the mixture and be drained from the bottom of the mixture leaving the purified sulfide stream.

In addition to removing $CS_2$ to unexpectedly low levels, caution can be applied to ensure that unacceptable amounts of additional impurities are not introduced into the purified sulfide stream as part of the purification processes disclosed herein. However, certain impurities may be present in the mercaptan source employed in the aqueous solution of the mercaptan and the base, and thereafter accumulate in the purified sulfide stream. Similarly, the exposure and interaction between the product stream and the aqueous phase may introduce water into the purified sulfide stream.

Thus, as discussed above in relation to the product stream, the purified sulfide stream also may contain amounts of methyl mercaptan, dimethyl disulfide, and/or water, and generally equal to, or not in excess of the ranges identified above. In certain aspects, processes may include additional steps to remove further impurities. For example, the purified sulfide stream may become saturated with 2000 ppmw water following the interaction between the product stream and the aqueous solution. In such aspects, processes can further comprise a step of drying the purified sulfide stream to form a dried sulfide product stream to form a dried sulfide product stream comprising a maximum amount of water of 2 wt. %, a maximum of 1 wt. %, a maximum of 2000 ppmw, a maximum of 1000 ppmw, a maximum of 500 ppmw, a maximum of 200 ppmw, a maximum of 100 ppmw, a maximum of 50 ppmw, or a maximum of 10 ppmw, by weight of the dried sulfide product stream. Alternatively, an amount of water in the dried sulfide product stream can be in a range from 1 to 1000 ppmw, from 10 to 500 ppmw, or from 50 to 200 ppmw, by weight of the dried sulfide product stream.

Considering all impurities present, the dried sulfide product stream can therefore comprise an amount of sulfide compound from 90 wt. % to 99.99 wt. %, from 95 wt. % to 99.99 wt. %, from 98 wt. % to 99.9 wt. %, or from 99 wt. % to 99.9 wt. %; alternatively, at least 99 wt. %, at least 99.9 wt. %, at least 99.99 wt. %, at least 99.995 wt. %, or at least 99.999 wt. %.

As discussed above, the removal of $CS_2$ from product streams containing a sulfide compound can be problematic due to the components having similar chemical and physical characteristics. Thus, the effectiveness of the removal step applied directly to $CS_2$ can be limited, with respect to both the relative amount of the $CS_2$ removed (compared to an amount of $CS_2$ present in the product stream) and the actual amount of $CS_2$ removed. Moreover, as the levels of $CS_2$ in the product stream are reduced, it can become increasingly difficult to remove any significant portion of $CS_2$ from the product stream where the chemical and/or physical properties are similar. In contrast, in the processes disclosed herein, all or substantially all of the $CS_2$ can be removed from the product stream to form a purified sulfide stream in an efficient manner via the use of an appropriate amount of a mercaptan to draw the $CS_2$ into an aqueous phase during a washing step.

The conditions and components disclosed herein can be combined in any manner to effectuate an efficient extraction of at least a portion of the $CS_2$ present in the product stream. Generally, at least 40 wt. % of the $CS_2$ in the product stream is extracted, and more often, at least 50 wt. %, at least 60 wt. %, at least 70 wt. %, at least 80 wt. %, at least 85 wt. %, at least 90 wt. %, at least 95 wt. %, or at least 98 wt. %, and in some instances, at least 99 wt. %, at least 99.9 wt. %, or at least 99.99 wt. %. Thus, typical amounts of the $CS_2$ in the product stream that are extracted from the organic phase can range from 60 wt. % to 99.99 wt. %, from 90 wt. % to 99.9 wt. %, or from 98 wt. % to 99.99 wt. %.

In certain aspects, the ratio of the concentration of $CS_2$ in the product stream prior to step (i) to the concentration of $CS_2$ in the purified sulfide stream can be at least 10:1, at least 25:1, or at least 100:1, and in some aspects, at least 250:1, at least 500:1, or at least 1000:1. With regard to the purity of the sulfide compound, the purified sulfide streams formed by the processes disclosed herein can contain amounts of $CS_2$ of less than or equal to 500 ppmw, less than or equal to 250 ppmw, less than or equal to 100 ppmw, less than or equal to 75 ppmw, less than or equal to 50 ppmw, less than or equal to 25 ppmw, less than or equal to 10 ppmw, or less than or equal to 5 ppmw (ppm by weight). Hence, the amount of CS$_2$ in the purified sulfide stream can range from 1 to 500 ppmw, from 1 to 100 ppmw, from 1 to 50 ppmw, from 10 to 500 ppmw, from 10 to 100 ppmw, or from 10 to 50 ppmw (ppm by weight), and the like. With respect to the overall purity of the sulfide compound in purified sulfide stream formed in step (ii), in certain aspects, the amount of the sulfide compound in the purified sulfide stream can be at least 99 wt. %, at least 99.9 wt. %, at least 99.99 wt. %, at least 99.995 wt. %, or at least 99.999 wt. %.

Similarly, the relative amount of the aqueous and organic phases present during step (i) can be within a particular range to efficiently remove CS$_2$ from the product stream. In certain aspects, a ratio of an amount of the aqueous solution of the mercaptide and the product stream during step (i) is in a range from 1:1 to 1:5, by weight. In certain aspects, the ratio can be at least 1:1, or at least 3:1; alternatively, less than 50:1, or less than 20:1; alternatively, in a range from 1:1 to 20:1, from 3:1 to 20:1, from 3:1 to 1:5, from 2:1 to 1:5, from 1:1 to 1:5, or from 1:2 to 1:4.

Optionally, any of the characteristics above correlated with the removal of CS$_2$ from the product stream, including the amount of CS$_2$ present in the product stream, can be monitored, and the amount of the mercaptan added to the product stream, and/or the duration of step (i), can be controlled accordingly. Additionally, or alternatively, the amount of CS$_2$ remaining in the purified sulfide stream may be monitored in the same fashion to provide indication of quality control and prevent excessive duration of step (i).

For instance, the processes disclosed herein can further comprise the steps of determining (or measuring) the concentration of the CS$_2$ present in the product stream and adjusting the amount of the mercaptan contacted with the product stream based on the concentration of CS$_2$ in the product stream (the determined concentration). In certain aspects, the amount of the aqueous solution contacted with the product stream may be adjusted. In other aspects, a concentration of the mercaptan within the aqueous solution may be adjusted. In still further aspects, it is contemplated that the duration of the contacting step may be adjusted to change the amount of the aqueous solution of the mercaptan and the base that contacts the product stream.

In any such aspects, a target amount of contact between the mercaptan and the product stream relative to the amount of CS$_2$ can be efficiently maintained to ensure substantially complete extraction of the CS$_2$ into the aqueous phase of the mixture formed during step (i) of the process, regardless of upward/downward spikes in the concentration of CS$_2$ in the product stream. Additionally, or alternatively, processes disclosed herein can further comprise steps of determining the concentration of CS$_2$ in the purified sulfide stream, and adjusting the amount of the mercaptan contacted with the product stream based on the concentration in the purified sulfide stream by mechanisms analogous to those described above.

It is further contemplated that the processes disclosed herein may be integrated within a continuous process.

Sulfide Compounds and Mercaptans

Generally, the product stream can contain any suitable sulfide compound in majority amount in which carbon disulfide also is present as an impurity, and thus may be benefit from the purification processes described herein. In some aspects, for instance, the product stream can contain a sulfide compound having formula (I):

$$R^1-S-R^2. \tag{I}$$

10

In formula (I), R$^1$ and R$^2$ independently can be a C$_1$ to C$_{18}$ substituted or unsubstituted, cycloalkyl group or linear or branched alkyl group. It is contemplated that R$^1$ and R$^2$ can be the same or different. When R$^1$ and R$^2$ are the same, the sulfide compound is symmetrical, and when R$^1$ and R$^2$ are different, the sulfide compound is asymmetrical.

R$^1$ in formula (I) can be a C$_1$ to C$_{18}$ substituted or unsubstituted, cycloalkyl group or linear or branched alkyl group. In one aspect, for example, R$^1$ can be a C$_1$ to C$_{14}$ substituted or unsubstituted, cycloalkyl group or linear or branched alkyl group, while in another aspect, R$^1$ can be a C$_1$ to C$_{12}$ substituted or unsubstituted, cycloalkyl group or linear or branched alkyl group, and in yet another aspect, R$^1$ can be a C$_1$ to C$_8$ substituted or unsubstituted, cycloalkyl group or linear or branched alkyl group. Consistent with aspects of the present invention, R$^1$ can be a cycloalkyl group; alternatively, R$^1$ can be a linear alkyl group; or alternatively, R$^1$ can be a branched alkyl group. Regardless of whether R$^1$ is a cyclic, linear, or branched alkyl group, R$^1$ can be unsubstituted, or can be substituted with any suitable substituent, any suitable number of substituents, and at any suitable position(s) that conforms to the rules of chemical valence.

R$^1$ can be a C$_1$ to C$_{18}$ linear or branched alkyl group in certain aspects of this invention. Thus, R$^1$ can be a C$_1$ to C$_{14}$ linear or branched alkyl group, a C$_1$ to C$_{12}$ linear or branched alkyl group, a C$_1$ to C$_8$ linear or branched alkyl group, or a C$_1$ to C$_6$ linear or branched alkyl group. Accordingly, in some aspects, R$^1$ can be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a decyl group, or a dodecyl group.

In other aspects, the alkyl group which can be R$^1$ in formula (I) can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-amyl group, a n-hexyl group, a n-heptyl group, a n-octyl group, or a n-dodecyl group; alternatively, a methyl group, an ethyl group, or an iso-propyl group; alternatively, a methyl group or an ethyl group; alternatively, a methyl group; alternatively, an ethyl group; alternatively, a n-propyl group; alternatively, an iso-propyl group; alternatively, a n-butyl group; alternatively, an iso-butyl group; alternatively, a sec-butyl group; alternatively, a tert-butyl group; alternatively, a n-pentyl group; alternatively, an iso-pentyl group; alternatively, a sec-pentyl group; alternatively, a neopentyl group; alternatively, a tert-amyl group; alternatively, a n-hexyl group; alternatively, a n-heptyl group; alternatively, a n-octyl group; or alternatively, or a n-dodecyl group.

R$^1$ can be a cycloalkyl group in certain aspects of this invention. Thus, R$^1$ can be a C$_3$ to C$_{18}$ cycloalkyl group, a C$_4$ to C$_{12}$ cycloalkyl group, a C$_4$ to C$_{10}$ cycloalkyl group, or a C$_8$ to C$_8$ cycloalkyl group. Accordingly, in some aspects, R$^1$ can be a cyclobutyl group, a cyclopentyl group, a cyclohexyl group, a cycloheptyl group, or a cyclooctyl group; alternatively, a cyclobutyl group; alternatively, a cyclopentyl group; alternatively, a cyclohexyl group; alternatively, a cycloheptyl group; or alternatively, a cyclooctyl group.

In accordance with another aspect of this invention, any alkyl group disclosed herein (cycloalkyl, linear alkyl, or branched alkyl) can be substituted with one or more substituents. Each non-hydrogen substituent(s) for the substituted alkyl group independently can be a $C_1$ to $C_{18}$ hydrocarbyl group; alternatively, a $C_1$ to $C_8$ hydrocarbyl group; or alternatively, a $C_1$ to $C_6$ hydrocarbyl group. Thus, the hydrocarbyl substituent can be a benzyl group, a phenyl group, a tolyl group, or a xylyl group, and the like, and, therefore, $R^1$ can be, for instance, a phenyl-substituted alkyl group. Additionally, the hydrocarbyl substituent can be a $C_1$ to $C_6$ linear or branched alkyl group and, therefore, $R^1$ can be, for instance, an alkyl-substituted cycloalkyl group, such as a methylcyclohexyl group.

Referring now to $R^2$ in formula (I), $R^2$ can be any $C_1$ to $C_{18}$ substituted or unsubstituted, cycloalkyl group or linear or branched alkyl group disclosed herein for $R^1$. Thus, for example, $R^2$ can be any cycloalkyl group, linear alkyl group, or branched alkyl group disclosed herein, and further, $R^2$ can be unsubstituted, or can be substituted with any suitable substituent or any substituent disclosed herein, any suitable number of substituents, and at any suitable position(s) that conforms to the rules of chemical valence.

In aspects where the sulfide compound is asymmetrical, the sulfide compound can be methyl ethyl sulfide, methyl iso-propyl sulfide, methyl dodecyl sulfide, ethyl octyl sulfide, n-pentyl n-heptyl sulfide, and the like, as well as any combination thereof. In certain aspects, the sulfide compound can be methyl ethyl sulfide. In aspects where the sulfide compound is symmetrical, the sulfide compound can be dimethyl sulfide, diethyl sulfide, di-n-propyl sulfide, di-iso-propyl sulfide, di-n-butyl sulfide, di-n-pentyl sulfide, di-n-hexyl sulfide, di-n-heptyl sulfide, di-n-octyl sulfide, di-n-dodecyl sulfide, and the like, as well as any combination thereof. In certain aspects, the sulfide compound can be dimethyl sulfide.

Mercaptans of the present disclosure can have structure similar to the sulfides described above, wherein one of $R^1$ and $R^2$ is H as a thiol group. Mercaptans therefore can adopt the structure as shown in formula (II):

$$R^3 \text{—} S \text{—} H. \qquad \text{(II)}$$

In formula (II), $R^3$ independently can be the same as disclosed for $R^1$ and $R^2$ above for formula (I). In certain aspects, $R^3$ can be a linear or branched alkyl group. It is contemplated that $R^3$ for the mercaptan can be the same or different from either or both of $R^1$ and $R^2$ in a sulfide present in the same process. In certain aspects, $R^3$ can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-amyl group, a n-hexyl group, a n-heptyl group, a n-octyl group, or a n-dodecyl group; alternatively, a methyl group, an ethyl group, or an iso-propyl group. In other aspects, $R^3$ can be ethyl, n-propyl, isopropyl, n-butyl, or sec-butyl; accordingly, the mercaptan can be methyl mercaptan, ethyl mercaptan, n-propyl mercaptan, isopropyl mercaptan, n-butyl mercaptan, or sec-butyl mercaptan.

Certain aspects of the processes disclosed herein may be applicable to sulfide compounds having particular characteristics, e.g., molecular weight, polarity, boiling point, etc. For instance, it can be beneficial for the sulfide compound to be a liquid (not a solid) and to remain in the liquid state at a particular set of process conditions, such as at standard temperature and pressure (STP, 1 atm and 20° C.). Thus, sulfide compounds suitable for the processes disclosed herein can be a liquid at STP, and beneficially remain a liquid at 0° C. and 2 atm, and/or remain a liquid at −10° C. and 2 atm. While not limited thereto, the sulfide compound can have a normal boiling point (at 1 atm) of at least 30° C., at least 50° C., at least 70° C., or at least 90° C. Additionally, or alternatively, the sulfide compound can have a normal boiling point within 100° C., within 50° C., within 30° C., or within 10° C., of that of carbon disulfide (which has a normal boiling point of ~46-47° C.).

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

The analytical procedures for determining the amount of various components in the Examples below were conducted as follows. The amount of carbon disulfide was determined by GC-SCD, the amount of MeSH, DMS, & dimethyl disulfide (DMDS) was determined by GC-FID, and the amount of water present was determined by GC-TCD.

Example 1

5,000 gallons of a dimethyl sulfide product stream was contaminated with 3 wt. % methyl mercaptan and transferred to a vertical tank designed for phase separation. Two aliquots of aqueous NaOH (20 wt. % NaOH, about 500 gallons each) were added to the vertical tank. The tank's contents were then mixed by using two pumps to circulate the material in the tank. The MeSH content was monitored for 24 hours, during which time the $CS_2$ content in the DMS was reduced from its initial value of about 2800 ppmw to less than 50 ppmw, as determined by GC-SCD according to the procedure described above. The aqueous phase was then separated from the organic phase containing DMS by draining the aqueous layer from the vertical tank containing the purified DMS product. The purified DMS product was then dried with molecular sieves. Surprisingly, not only was the MeSH removed to yield DMS with an acceptable purity of greater 99%, but it was also observed that the $CS_2$ concentration had been reduced to less than 10 ppmw.

Examples 2-4

Figure 2:
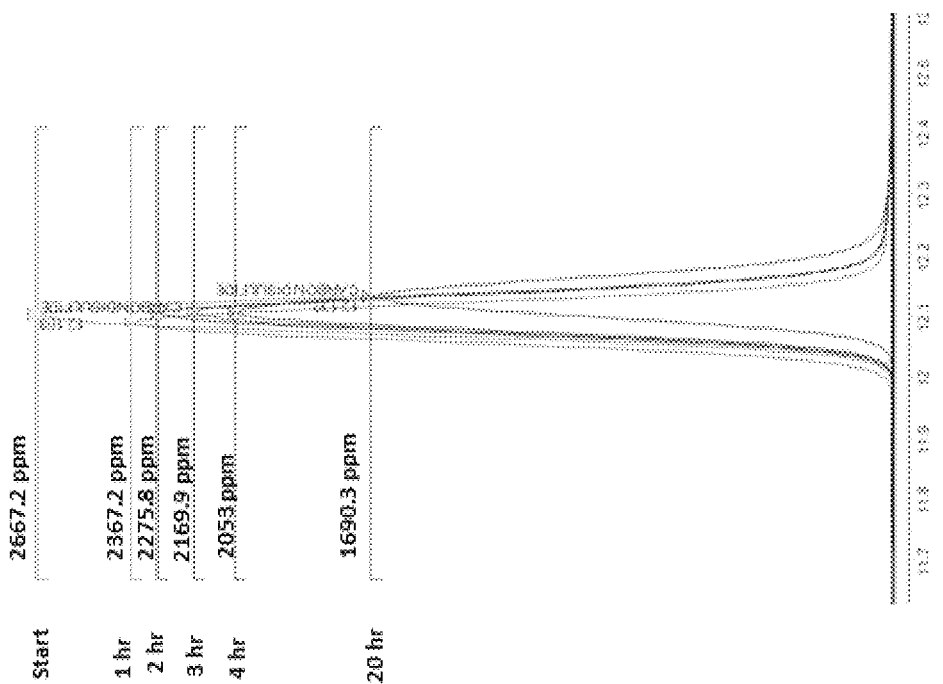
FIG. 2 presents gas chromatograms comparing the decrease in $CS_2$ content over time for Examples 3 and 4.
Figure 2:
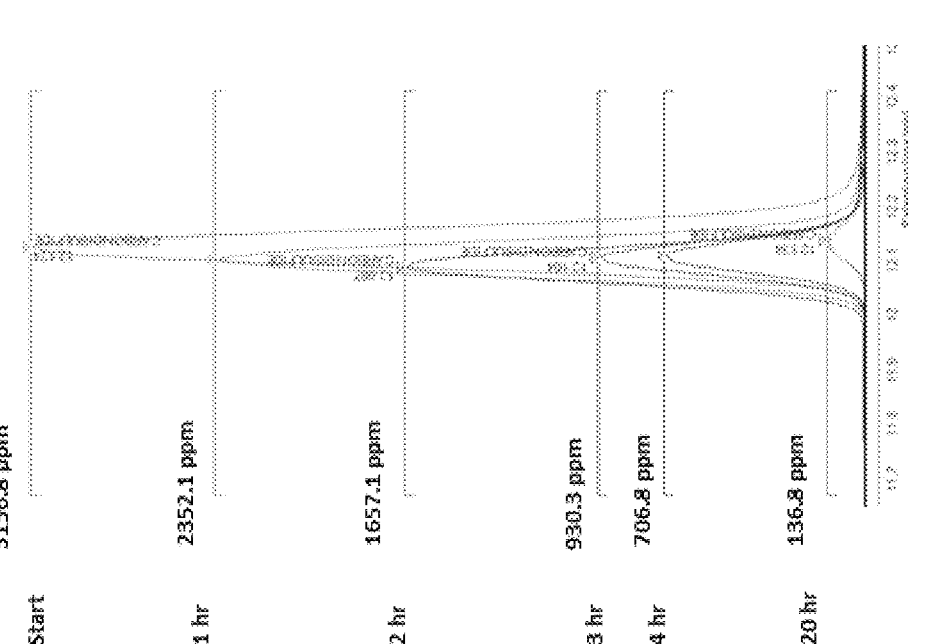

The results of Example 1 were explored further in a series of lab scale experiments. In Example 2, a 50:50 wt. % mixture of aqueous NaOH (8% wt. %) and a DMS product containing 0.8 wt. % MeSH and 3156 ppmw of $CS_2$ were mixed together overnight. The $CS_2$ content of the organic phase of the mixture was analyzed by GC-SCD. Within 24 hours of mixing, the organic phase of the mixture contained only 65 ppmw $CS_2$, as shown in FIG. 2.

Examples 3-4 were performed using a 75:25 wt. % mixture of DMS and aqueous NaOH (8 wt. %). Example 3 was conducted using a DMS mixture a having relatively high amount of MeSH, 0.8 wt. %. Example 4 was conducted using a DMS mixture having a low amount of MeSH, less than 0.2 wt. %. The $CS_2$ content in the initial DMS mixtures for each of Examples 3 and 4 was about 3000 ppmw. Aqueous NaOH was added to the respective DMS mixtures as described above, over a period of 24 hours. The organic phases of each mixture were sampled and analyzed for $CS_2$ content on the GC-SCD at several times during 24 hours.

The results for Examples 3 and 4 are presented below in Table 1 shows the $CS_2$ content results as the two DMS product samples were being treated throughout the mixing step. FIG. 2 shows the GC-SCD chromatogram of the $CS_2$ content in DMS samples during the caustic treatments. As shown, the $CS_2$ content in the high mercaptan DMS sample (containing 0.8 wt. % MeSH) decreased at a faster rate than $CS_2$ content in the low mercaptan DMS sample (containing less than 0.2 wt. % MeSH). Further, Examples 2 and 3 showed a drastically more complete removal of $CS_2$ to result in a highly pure DMS product containing roughly ten times less $CS_2$ than compared to Example 4 having a reduced amount of MeSH present.

TABLE 1

| | DMS with ~0.8 wt. % MeSH | DMS with <0.2 wt. % MeSH |
|---|---|---|
| Hour | ($CS_2$ ppmw) | ($CS_2$ ppmw) |
| 0 | 3156.8 | 2667.2 |
| 1 | 2352.1 | 2367.2 |
| 2 | 1657.1 | 2275.8 |
| 3 | 930.3 | 2169.9 |
| 4 | 706.8 | 2053.2 |
| 20 | 136.8 | 1690.3 |

$CS_2$ content of Examples 3-4 vs time.

Example 5

Figure 3:
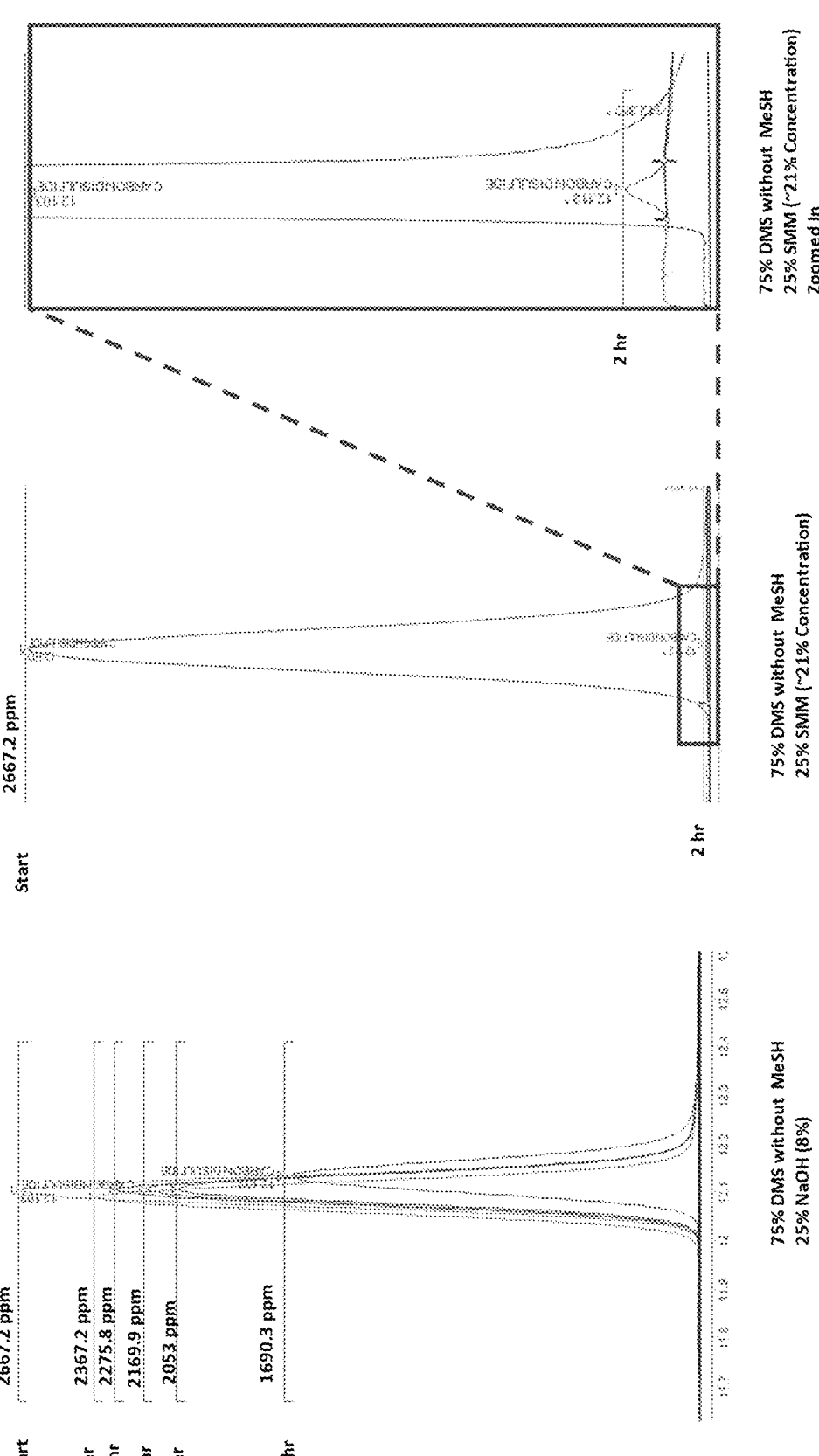
FIG. 3 presents gas chromatograms comparing the decrease in $CS_2$ content over time for Examples 3 and 5.

Based on the results observed in Examples 1-4, it was theorized that the activity of methyl mercaptan in removing $CS_2$ from the organic phase into the aqueous phase (e.g., as a phase transfer agent) may occur by formation of sodium methyl mercaptide (SMM) through reaction of MeSH with NaOH. Example 5 was performed according to the same method of Examples 3-4, using a 75/25 wt. % mixture of the low MeSH DMS used in Example 4 and adding an aqueous mixture of 21 wt. % sodium methyl mercaptide. This mixture was analyzed for $CS_2$ concentration after 2 hours of mixing. The resulting $CS_2$ concentration was below 20 ppmw. The GC-SCD chromatogram shown in FIG. 3 compares the hourly results of $CS_2$ removal observed during Example 5, with those of Example 4 lacking the additional sodium methyl mercaptide. Surprisingly, the $CS_2$ for Example 5 was practically completely removed from the organic phase after two hours mixing in the presence of sodium methyl mercaptan.

Examples 6-33

In addition to its exceptional performance in removing $CS_2$ as demonstrated above, an aqueous solution of sodium methyl mercaptide (SMM) also provides a practical pathway for adding MeSH to DMS for removal of $CS_2$, as it is readily available and economical. However, while performing an extraction using aqueous 21% SMM was shown to eliminate the $CS_2$ from DMS (Example 5), it also has potential to add other impurities (e.g., water, MeSH, and DMDS) to the DMS. To better understand how much SMM would be needed to remove $CS_2$ and to what extent additional impurities may accumulate, a series of SMM washes were performed.

An aqueous solution of 21% SMM was diluted with 21 wt. % aqueous NaOH to produce a series of SMM dilutions between 0.5 and 21% SMM by weight that were then used to extract $CS_2$. The effectiveness of caustic washes using each SMM dilution (0.5%, 1%, 2%, 5%, 10% and 21% SMM (no dilution)) was evaluated according to the following procedure. The effectiveness of caustic washes (21% aqueous NaOH) without SMM present (e.g., Example 6, 0% SMM) was also evaluated.

First, an appropriate amount of SMM dilution and DMS were added to a 100 mL bottle with a total volume of 50 mL. The two phases were mixed vigorously for four hours and then allowed to sit for 10 minutes and separate into a lower aqueous phase and an upper organic phase. The aqueous layer was removed from the mixture, leaving the organic layer. The resulting organic layer was then analyzed via GC-SCD, GC-FID, and GC-TCD. The GC-SCD is to measure $CS_2$, GC-FID is used to measure MeSH, DMS, & DMDS, and the GC-TCD is used to measure water. The results for each of Examples 6-33 are presented below in Table 2.

As expected from the results of Examples 1-5, it was again observed that increasing the ratio of SMM generally improved the extent to which $CS_2$ was removed from the organic phase. However, removal of $CS_2$ was less effective for Examples 13-19 where the amount of the aqueous phase relative to the organic phase was less than about 10% of the total mixture, and ineffective where the aqueous phase accounted for only 5% of the mixture. Increasing the ratio of the aqueous phase increased the efficiency of $CS_2$ removal from the organic phase. Also as shown in Table 2, the amount of water present for each of the product mixtures was relatively constant, having concentrations of water in the range of 0.17 to 0.20 wt. %, and showing that the DMS products were quickly saturated with water when accompanied by even a small amount of mercaptan.

TABLE 2

Amount of $CS_2$ and other impurities remaining in Examples 6-33.

| Example | Phase Ratio (DMS:aqueous) | SMM (wt. %) | $CS_2$ (ppmw) | MeSH (wt. %) | DMS (wt. %) | DMDS (wt. %) | Water (wt. %) |
|---|---|---|---|---|---|---|---|
| 6 | 95:5 | 0 | 1743 | 0.0789 | 99.74 | 0.0057 | 0.014 |
| 7 | 95:5 | 0.5 | 1575 | 0.006 | 99.85 | 0.0127 | 0.1648 |
| 8 | 95:5 | 1 | 1635 | 0.006 | 99.85 | 0.009 | 0.1629 |
| 9 | 95:5 | 2 | 1524 | 0.007 | 99.86 | 0.009 | 0.1673 |
| 10 | 95:5 | 5 | 1209 | 0.011 | 99.84 | 0.009 | 0.1713 |
| 11 | 95:5 | 10 | 1009 | 0.0204 | 99.85 | 0.0108 | 0.1751 |
| 12 | 95:5 | 21 | 1403 | 0.157 | 99.7 | 0.013 | 0.194 |
| 13 | 90:10 | 0 | 1743 | 0.0789 | 99.74 | 0.0057 | 0.014 |
| 14 | 90:10 | 0.5 | 1513 | 0.006 | 99.83 | 0.01214 | 0.1667 |
| 15 | 90:10 | 1 | 1347 | 0.006 | 99.86 | 0.009 | 0.1654 |
| 16 | 90:10 | 2 | 1347 | 0.006 | 99.86 | 0.009 | 0.1654 |

US 12,655,097 B2

15

16

TABLE 2-continued

| | | | | | | | |
|---|---|---|---|---|---|---|---|
| | Amount of CS$_2$ and other impurities remaining in Examples 6-33. | | | | | | |
| Example | Phase Ratio (DMS:aqueous) | SMM (wt. %) | CS$_2$ (ppmw) | MeSH (wt. %) | DMS (wt. %) | DMDS (wt. %) | Water (wt. %) |
| 17 | 90:10 | 5 | 996 | 0.01 | 99.82 | 0.013 | 0.1721 |
| 18 | 90:10 | 10 | 863 | 0.0186 | 99.81 | 0.0151 | 0.179 |
| 19 | 90:10 | 21 | 198 | 0.1912 | 99.6 | 0.024 | 0.198 |
| 20 | 75:25 | 0 | 1743 | 0.0789 | 99.74 | 0.0057 | 0.014 |
| 21 | 75:25 | 0.5 | 1090 | 0.005 | 99.82 | 0.02745 | 0.17528 |
| 22 | 75:25 | 1 | 673 | 0.005 | 99.58 | 0.034 | 0.1689 |
| 23 | 75:25 | 2 | 740 | 0.005 | 99.79 | 0.031 | 0.1952 |
| 24 | 75:25 | 5 | 183 | 0.009 | 99.82 | 0.034 | 0.1739 |
| 25 | 75:25 | 10 | 7 | 0.01927 | 99.8 | 0.04402 | 0.1924 |
| 26 | 75:25 | 21 | 5 | 0.2803 | 99.5 | 0.072 | 0.2092 |
| 27 | 50:50 | 0 | 1743 | 0.0789 | 99.74 | 0.0057 | 0.014 |
| 28 | 50:50 | 0.5 | 692 | 0.005 | 99.8 | 0.063 | 0.1756 |
| 29 | 50:50 | 1 | 274 | 0.005 | 99.76 | 0.07 | 0.169 |
| 30 | 50:50 | 2 | 478 | 0.005 | 99.77 | 0.072 | 0.1947 |
| 31 | 50:50 | 5 | 20 | 0.00925 | 99.77 | 0.078 | 0.1741 |
| 32 | 50:50 | 10 | 0 | 0.01902 | 99.7 | 0.1187 | 0.19245 |
| 33 | 50:50 | 21 | 8 | 0.3661 | 99.26 | 0.21949 | 0.2073 |

With respect to the amount of the mercaptan remaining in the organic phase, Examples having the highest amount of MeSH applied during the extraction (21% MeSH) resulted in a sharp increase in the amount of residual mercaptan in the product. However, surprisingly, products where the SMM concentrations were 10% SMM or lower did not contain a significantly higher amount of the mercaptan.

The concentration of DMDS in the products gradually increased with how much SMM that was added. However, the amount of DMDS introduced to the DMS product remained relatively low even at the highest concentrations of SMM.

In sum, the SMM treatments at concentrations of 10% SMM or greater were most effective for the removal of CS$_2$, provided that the aqueous phase was greater than 10% of the mixture. Increasing the concentration of SMM to 21% was not shown to improve the CS$_2$ removal dramatically and began to reduce the resulting purity by introduction of MeSH impurity remaining in the product.

An adequate continuous process to remove CS$_2$ from DMS via caustic treatment should be considered with an appropriate phase separation step that would minimize or prevent high chemical oxygen demand (COD) during aqueous phase draining. A continuous stirred tank reactor can be used for conducting the caustic treatment and a downstream separator (e.g., a liquid-liquid extractor) can be used for phase separation.

Aspects

The invention is described above with reference to numerous aspects and embodiments, and specific examples. Many variations will suggest themselves to those skilled in the art in light of the above detailed description. All such obvious variations are within the full intended scope of the appended claims. Other aspects of the invention can include, but are not limited to, the following (aspects typically are described as "comprising" but, alternatively, can "consist essentially of" or "consist of" unless specifically stated otherwise):

Aspect 1. A process to purify a product stream containing a sulfide compound and CS$_2$, the process comprising (i) contacting the product stream with an aqueous solution comprising a mercaptan and a base to form a mixture, and (ii) removing at least a portion of an aqueous layer from the mixture to form a purified sulfide stream.

Aspect 2. The process defined in aspect 1, wherein the process further comprises a step of (iii) drying the purified sulfide stream to form a dried sulfide product stream.

Aspect 3. The process defined in aspect 1 or 2, wherein the sulfide compound has formula (I): R$^1$—S—R$^2$ (I); wherein R$^1$ and R$^2$ independently are a C$_1$ to C$_{18}$ substituted or unsubstituted, cycloalkyl group or linear or branched alkyl group.

Aspect 4. The process defined in aspect 3, wherein R$^1$ and R$^2$ independently are a branched alkyl group.

Aspect 5. The process defined in aspect 3, wherein R$^1$ and R$^2$ independently are a linear alkyl group.

Aspect 6. The process defined in aspect 3, wherein R$^1$ and R$^2$ independently are a substituted alkyl group (e.g., a phenyl-substituted alkyl group).

Aspect 7. The process defined in any one of aspects 3-6, wherein R$^1$ and R$^2$ independently are a C$_1$ to C$_{12}$ alkyl group.

Aspect 8. The process defined in aspect 3, wherein R$^1$ and R$^2$ independently are a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group.

Aspect 9. The process defined in aspect 3, wherein R$^1$ and R$^2$ independently are a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, or a tert-amyl group.

Aspect 10. The process defined in aspect 3, wherein R$^1$ and R$^2$ independently are a methyl group or an ethyl group.

Aspect 11. The process defined in any one of aspects 3-10, wherein R$^1$ and R$^2$ are different.

Aspect 12. The process defined in any one of aspects 3-10, wherein R$^1$ and R$^2$ are the same.

Aspect 13. The process defined in aspect 1 or 2, wherein the sulfide compound is methyl ethyl sulfide, methyl iso-propyl sulfide, methyl dodecyl sulfide, ethyl octyl sulfide, n-pentyl n-heptyl sulfide, or any combination thereof.

Aspect 14. The process defined in aspect 1 or 2, wherein the sulfide compound is methyl ethyl sulfide.

Aspect 15. The process defined in aspect 1 or 2, wherein the sulfide compound is dimethyl sulfide, diethyl sulfide, di-n-propyl sulfide, di-iso-propyl sulfide, di-n-butyl sulfide, di-n-pentyl sulfide, di-n-hexyl sulfide, di-n-heptyl sulfide, di-n-octyl sulfide, di-n-dodecyl sulfide, or any combination thereof.

Aspect 16. The process defined in aspect 1 or 2, wherein the sulfide compound is dimethyl sulfide.

Aspect 17. The process defined in any one of aspects 1-16, wherein the product stream comprises any wt. % of the sulfide compound disclosed herein, e.g., at least 85 wt. %, at least 90 wt. %, at least 95 wt. %, at least 98 wt. %, at least 99 wt. %, from 95 wt. % to 99.99 wt. %, or from 98 wt. % to 99.9 wt. %.

Aspect 18. The process defined in any one of aspects 1-17, wherein the product stream comprises any minimum amount of $CS_2$ disclosed herein, e.g., a minimum of 250 ppmw, a minimum of 500 ppmw, or a minimum of 1000 ppmw (by weight).

Aspect 19. The process defined in any one of aspects 1-18, wherein the product stream comprises an amount of $CS_2$ in any range disclosed herein, e.g., from 250 to 5000 ppmw, from 500 ppmw to 10,000 ppmw, from 1000 to 5000 ppmw, or from 2000 to 4000 ppmw (by weight).

Aspect 20. The process defined in any one of aspects 1-19, wherein the product stream (or purified sulfide product stream) further comprises an amount of $H_2S$, an amount of methyl mercaptan, an amount of dimethyl disulfide, or an amount of water in any range disclosed herein, e.g., from 1 to 100 ppmw, from 100 ppmw to 250 ppmw, from 50 ppmw to 500 ppmw, or from 250 to 2500 ppmw (ppm by weight).

Aspect 21. The process of any one of aspects 1-20, wherein the mercaptan is an alkylmercaptan (e.g., methyl mercaptan, ethyl mercaptan, n-propyl mercaptan, isopropyl mercaptan, n-butyl mercaptan, sec-butyl mercaptan).

Aspect 22. The process defined in any one of aspects 1-21, wherein the base comprises sodium hydroxide, potassium hydroxide, calcium hydroxide, ammonium hydroxide, or any combination thereof.

Aspect 23. The process defined in aspect 22, wherein the base comprises sodium hydroxide.

Aspect 24. The process defined in any one of aspects 1-23, wherein the aqueous solution comprising the mercaptide has a pH in any range disclosed herein, e.g., at least 9, at least 9.5, at least 10, at least 11, from 9 to 14, from 10 to 14, or from 10 to 13.

Aspect 25. The process defined in any one of aspects 1-24, wherein the aqueous solution of the mercaptan and the base is formed as an aqueous solution of a mercaptide.

Aspect 26. The process of aspect 25, wherein the mercaptide is a sodium salt of the mercaptan, or a potassium salt of the mercaptan.

Aspect 27. The process of aspect 25, wherein the mercaptide comprises sodium methyl mercaptide.

Aspect 28. The process defined in any one of aspects 1-27, wherein step (i) is conducted at a temperature in any suitable range or any range disclosed herein, e.g., from 0° C. to 40° C., from 10° C. to 35° C., or from 15° C. to 30° C.

Aspect 29. The process defined in any one of aspects 1-28, wherein step (i) is conducted at a pressure in any suitable range or any range disclosed herein, e.g., from ambient to 100 psig (689 kPag), or from 5 to 60 psig (34 to 414 kPag).

Aspect 30. The process defined in any one of aspects 1-29, wherein in step (i), a molar ratio of mercaptan:$CS_2$ in the mixture is in any suitable range or any range disclosed herein, e.g., from 1:1 to 50:1, from 1.5:1 to 30:1, or from 2:1 to 20:1.

Aspect 31. The process defined in any one of aspects 1-30, wherein in step (i), an amount of the mercaptide in the aqueous solution contacted with the product stream is in any suitable range or any range disclosed herein, e.g., from 0.1 to 50 wt. %, from 1 to 70 wt. %, from 10 to 70 wt. %, from 1 to 30 wt. %, or from 5 to 15 wt. %, based on the total weight of the mixture.

Aspect 32. The process defined in any one of aspects 1-31, wherein a ratio of an amount (by weight) of the aqueous solution of the mercaptan and the base relative to an amount of the product stream (by weight) is in a range from 3:1 to 1:5, from 2:1 to 1:5, from 1:1 to 1:5, or from 1:2 to 1:4.

Aspect 33. The process defined in any one of aspects 1-32, wherein step (i) is conducted for a time period in any suitable range or any range disclosed herein, e.g., from 1 min to 24 hr, from 1 hr to 12 hr, or from 2 hr min to 8 hr.

Aspect 34. The process defined in any one of aspects 1-33, wherein in step (i), contacting the product stream with the aqueous solution of the mercaptide comprises agitating the mixture.

Aspect 35. The process defined in any one of aspects 1-34, wherein in step (ii), the at least a portion of the aqueous layer is removed from the mixture using any suitable technique or any technique disclosed herein, e.g., extracting, centrifuging, filtering, decanting, draining, evaporating, distilling, or any combination thereof, to form the purified sulfide stream.

Aspect 36. The process defined in any one of aspects 1-35, wherein the purified sulfide stream comprises any wt. % of the sulfide compound disclosed herein, e.g., at least 95 wt. %, at least 98 wt. %, at least 99 wt. %, at least 99.5 wt. %, at least 99.9 wt. %, at least 99.99 wt. %, or at least 99.995 wt. %.

Aspect 37. The process defined in any one of aspects 1-36, wherein the purified sulfide stream comprises an amount of $CS_2$ in any range disclosed herein, e.g. a maximum of 1000 ppmw, a maximum of 500 ppmw, a maximum of 200 ppmw, a maximum of 100 ppmw, a maximum of 50 ppmw, a maximum of 20 ppmw, a maximum of 10 ppmw, in a range from 1 to 500 ppmw, from 1 to 100 ppmw, from 1 to 50 ppmw, from 10 to 500 ppmw, from 10 to 100 ppmw, or from 10 to 50 ppmw (ppm by weight).

Aspect 38. The process defined in any one of aspects 1-37, wherein prior to step (i), a ratio of a ppmw concentration of $CS_2$ present in the product stream to the ppmw concentration of $CS_2$ present in the purified sulfide stream is in any range disclosed herein, e.g., at least 10:1, at least 25:1, at least 100:1, or at least 500:1.

Aspect 39. The process defined in any one of aspects 2-38, wherein in step (iii), drying the purified sulfide stream uses any suitable technique or any technique disclosed herein, e.g., heating, evaporating, distilling, or any combination thereof, to form the dried sulfide product stream.

Aspect 40. The process defined in any one of aspects 2-39, wherein the dried sulfide product stream comprises any wt. % of the sulfide compound disclosed herein, e.g., at least 95 wt. %, at least 98 wt. %, at least 99 wt. %, at least 99.5 wt. %, at least 99.9 wt. %, at least 99.99 wt. %, or at least 99.995 wt. %.

Aspect 41. The process defined in any one of aspects 2-40, wherein the dried sulfide product stream comprises an amount of moisture (water) in any range disclosed herein, e.g., a maximum of 2 wt. %, a maximum of 1 wt. %, a maximum of 1000 ppmw, a maximum of 500 ppmw, a maximum of 200 ppmw, a maximum of 100 ppmw, a maximum of 50 ppmw, in a range from 1 to 1000 ppmw, or in a range from 10 to 200 ppmw (by weight).

Aspect 42. The process defined in any one of aspects 1-41, further comprising the steps of (a) determining a concentration of the $CS_2$ in the product stream, and (b) adjusting an amount of the mercaptan contacted with the product stream based on the concentration of the $CS_2$ in the product stream.

Aspect 43. The process defined in any one of aspects 1-42, further comprising the steps of (A) determining a concentration of the $CS_2$ in the purified sulfide stream (or the dried sulfide product stream), and (B) adjusting an amount of the mercaptan contacted with the product stream based on the concentration of the $CS_2$ in the purified sulfide stream (or the dried sulfide product stream).

Aspect 44. The process defined in aspect 42 or 43, wherein determining a concentration of $CS_2$ in DMS comprises analyzing a DMS sample using gas chromatography with a sulfur chemiluminescence detector.

Aspect 45. The process defined in any one of aspects 1-44, wherein the process is a continuous process.

Aspect 46. The process defined in aspect 45, wherein step (i) is conducted in a continuous stirred tank reactor, and step (ii) is conducted in separation vessel.

We claim:

1. A process to purify a product stream containing at least 80 wt. % of a sulfide compound and $CS_2$, the process comprising:
   (i) contacting the product stream with an aqueous solution comprising a mercaptan and a base to form a mixture; and
   (ii) removing at least a portion of an aqueous layer from the mixture to form a purified sulfide stream; wherein the sulfide compound has formula (I):

$$R^1 - S - R^2; \tag{I}$$

R1 and R2 independently are selected from the group consisting of a $C_1$ to $C_{18}$ substituted or unsubstituted, cycloalkyl group and linear or branched alkyl group;
   and wherein the base is selected from the group consisting of sodium hydroxide, potassium hydroxide, calcium hydroxide, ammonium hydroxide, and any combination thereof.

2. The process of claim 1, wherein the process further comprises a step of (iii) drying the purified sulfide stream to form a dried sulfide product stream.

3. The process of claim 2, wherein the dried sulfide product stream comprises:
   at least 99 wt. % of the sulfide compound; and
   less than or equal to 1000 ppmw of water.

4. The process of claim 1, wherein the sulfide compound is methyl ethyl sulfide.

5. The process of claim 1, wherein the sulfide compound is dimethyl sulfide.

6. The process of claim 1, wherein the product stream comprises:
   at least 98 wt. % of the sulfide compound; and
   from 500 ppmw to 10,000 ppmw of the $CS_2$.

7. The process of claim 1, wherein the aqueous solution comprising the mercaptan and the base comprises an aqueous solution of a mercaptide.

8. The process of claim 7, wherein the mercaptide comprises sodium methyl mercaptide.

9. The process of claim 1, wherein in step (i):
   a molar ratio of mercaptan:$CS_2$ in the mixture is in a range from 1:1 to 50:1;
   an amount of the aqueous solution contacted with the product stream is in a range from 1 to 70 wt. %, based on a total weight of the mixture;

a weight ratio of an amount of the aqueous solution relative to an amount of the product stream is in a range from 3:1 to 1:5; or
   any combination thereof.

10. The process of claim 1, wherein:
   contacting the product stream with the aqueous solution comprises agitating the mixture; and
   removing the at least a portion of the aqueous layer from the mixture comprises extracting, centrifuging, filtering, decanting, draining, evaporating, distilling, or any combination thereof.

11. The process of claim 1, wherein the purified sulfide stream comprises at least 99 wt. % of the sulfide compound.

12. The process of claim 1, wherein:
   the purified sulfide stream comprises from 1 to 500 ppmw of the $CS_2$; and/or
   a ratio of a ppmw concentration of $CS_2$ present in the product stream prior to step (i) to a ppmw concentration of $CS_2$ present in the purified sulfide stream is at least 10:1.

13. The process of claim 1, further comprising the steps of:
   (a) determining a concentration of the $CS_2$ in the product stream; and
   (b) adjusting an amount of the mercaptan contacted with the product stream based on the concentration of the $CS_2$ in the product stream.

14. The process of claim 13, wherein determining the concentration of $CS_2$ in the product stream comprises analyzing a sample of the product stream using gas chromatography and a sulfur chemiluminescence detector.

15. The process of claim 1, further comprising the steps of:
   (A) determining a concentration of the $CS_2$ in the purified sulfide stream; and
   (B) adjusting an amount of the mercaptan contacted with the product stream based on the concentration of the $CS_2$ in the purified sulfide stream.

16. The process of claim 1, wherein step (i) is conducted in a continuous stirred tank reactor, and step (ii) is conducted in separation vessel.

17. The process of claim 1, wherein the mercaptan is selected from the group consisting of methyl mercaptan, ethyl mercaptan, n-propyl mercaptan, isopropyl mercaptan, n-butyl mercaptan, sec-butyl mercaptan, and any combination thereof.

18. A process to purify a product stream containing at least 80 wt. % of a sulfide compound and $CS_2$, the process comprising:
   (i) contacting the product stream with an aqueous solution comprising a mercaptan and a base to form a mixture; and
   (ii) removing at least a portion of an aqueous layer from the mixture to form a purified sulfide stream;
   wherein the sulfide compound is selected from the group consisting of methyl ethyl sulfide, methyl iso-propyl sulfide, methyl dodecyl sulfide, ethyl octyl sulfide, n-pentyl n-heptyl sulfide, dimethyl sulfide, diethyl sulfide, di-n-propyl sulfide, di-iso-propyl sulfide, di-n-butyl sulfide, di-n-pentyl sulfide, di-n-hexyl sulfide, di-n-heptyl sulfide, di-n-octyl sulfide, di-n-dodecyl sulfide, and any combination thereof; and
   wherein the base is selected from the group consisting of sodium hydroxide, potassium hydroxide, calcium hydroxide, ammonium hydroxide, and any combination thereof.

19. The process of claim 18, wherein:

the process further comprises a step of (iii) drying the purified sulfide stream to form a dried sulfide product stream; and the dried sulfide product stream comprises at least 99 wt. % of the sulfide compound and less than or equal to 1000 ppmw of water.

20. The process of claim 18, wherein:

the product stream comprises at least 98 wt. % of the sulfide compound and from 500ppmw to 10,000 ppmw of the $CS_2$; and the purified sulfide stream comprises at least 99 wt. % of the sulfide compound and a maximum of 200 ppmw of the $CS_2$.

21. The process of claim 20, wherein the sulfide compound is methyl ethyl sulfide or dimethyl sulfide.

22. The process of claim 21, wherein the mercaptan is selected from the group consisting of methyl mercaptan, ethyl mercaptan, n-propyl mercaptan, isopropyl mercaptan, n-butyl mercaptan, sec-butyl mercaptan, and any combination thereof.

23. The process of claim 21, wherein the aqueous solution comprising the mercaptan and the base comprises an aqueous solution of a mercaptide.

* * * * *